US006956212B2

(12) United States Patent
Todokoro

(10) Patent No.: US 6,956,212 B2
(45) Date of Patent: Oct. 18, 2005

(54) ELECTRON MICROSCOPE OBSERVATION SYSTEM AND OBSERVATION METHOD

(75) Inventor: Hideo Todokoro, Hinode-machi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/963,815

(22) Filed: Oct. 14, 2004

(65) Prior Publication Data

US 2005/0061975 A1 Mar. 24, 2005

Related U.S. Application Data

(63) Continuation of application No. 10/333,782, filed on Jan. 24, 2003, now Pat. No. 6,822,232.

(51) Int. Cl.⁷ .............................................. G01N 23/00
(52) U.S. Cl. ...................... 250/310; 250/307
(58) Field of Search ............................ 250/252.1, 306, 250/307, 310, 311

(56) References Cited

U.S. PATENT DOCUMENTS 6,822,232 B1 * 11/2004 Todokoro .................... 250/310

FOREIGN PATENT DOCUMENTS

| JP | 9-63529 | 3/1997 | | |
|----|---------|--------|----|----|
| JP | 09-063529 | 3/1997 | | |
| JP | 09-063529 | * 7/1997 | ............ | H01J/37/22 |
| JP | 11-103291 | 4/1999 | | |
| JP | 2000-040112 | 2/2000 | | |
| JP | 2000-123770 | 4/2000 | | |
| JP | 2000-149849 | 5/2000 | | |
| JP | 2000-340156 | 8/2000 | | |
| JP | 2000-340156 | * 12/2000 | ............ | H01J/37/26 |
| JP | 2001-43821 | 2/2001 | | |
| JP | 2001-043821 | * 2/2001 | ............ | H01J/37/24 |
| JP | 2003-060802 | * 2/2003 | .......... | H04M/11/00 |

* cited by examiner

Primary Examiner—Frank G. Font
Assistant Examiner—Christopher M. Kalivoda
(74) Attorney, Agent, or Firm—Dickstein Shapiro Morin & Oshinsky LLP

(57) ABSTRACT

An electron microscope observation system and an observation method are provided. The electron microscope observation system and the observation method can reduce initial investment, and can eliminate burden of maintenance of the apparatus, and can easily and appropriately perform preparation of a sample.

An electron microscope, an image display unit of an electron microscope center side for displaying an image of image signals obtained by irradiating electrons on a sample using the electron microscope, a transmission path for transmitting the image signals and an image display unit of an operation center side for displaying a screen of the electron microscope by the image signals are provided, and an observation appointment and approval screen is displayed on the two image display units, and the sample preparation-processed in the observation center side based on an instruction given from the operation center is loaded, and observation of the sample is executed based on sample observation condition information to output image information, and the observation image is displayed on the two image display unites, and charge processing is executed based on a content level of the observation including preparation processing of the sample and occupying hours of the electron microscope to display the charge processing result.

6 Claims, 5 Drawing Sheets

ELECTRON MICROSCOPE OBSERVATION SYSTEM AND OBSERVATION METHOD

CROSS-REFERENCE TO RELATED APPLICATION

This application is a continuation of U.S. patent application Ser. No. 10/333,782, filed on Jan. 24, 2003 now U.S. Pat. No. 6,822,232 the subject matter of which is incorporated in its entirety by reference herein.

TECHNICAL FIELD

The present invention relates to an electron microscope observation system, and particularly to a charge requisition system when an electron microscope is used through remote operation.

BACKGROUND ART

An example of using an electron microscope through remote operation is disclosed in Japanese Patent Application Laid-Open No.9-63529. The gazette discloses an electron microscope observation system comprising an electron microscope main body; a converting unit for converting various electron beam scanning speeds to an image scanning speed, and making the image scanning speed in synchronism with a transmission path; an analogue-digital converter for converting analogue image signals to digital image signals; a digital-analogue converter for digital image signals to analogue image signals; and an image display unit for displaying electron microscope image signals, and further comprising an electron microscope operation unit for performing operation of moving a sample stage, operation of changing the magnification and operation of focusing of the electron microscope main body; and an operation signal input unit for inputting the operation control signal to the electron microscope operation unit.

DISCLOSURE OF INVENTION

An object of the present invention is to provide an electron microscope observation system and an electron microscope observation method which can reduce initial investment, and can eliminate burden of maintenance of the apparatus, and can easily and appropriately perform preparation of a sample.

The present invention provides an electron microscope observation system comprising an electron microscope, an image display unit of an electron microscope center side for displaying an image of image signals obtained by irradiating electrons on a sample using the electron microscope, a transmission path for transmitting the image signals and an image display unit of an operation center side for displaying a screen of the electron microscope by the image signals, and performing operation of moving a sample stage, operation of changing magnification and operation of focusing of the electron microscope, wherein the electron microscope observation system displays an observation appointment and approval screen on the two image display units, specifying observation conditions of the sample from the operation center side to the observation center side through the transmission path, executing observation of the sample processed based on the observation conditions in the observation center side to output image information, displaying the observation image on said two image display units, also displaying a content level of the observation including the observation conditions of the sample and occupying hours of the electron microscope on the two image display units. The electron microscope observation system also executes charge processing based on the content level and the occupying hours and displays the charge processing result depending on cases. The "specifying" described above includes setting of observation conditions or instructing observation conditions to the observation center side.

Further, the present invention provides an electron microscope observation method using an electron microscope observation system displaying an image of image signals obtained by irradiating electrons on a sample using an electron microscope, the method comprising the steps of displaying an observation appointment and approval screen on two image display units in an observation center side and in an operation center side, sending the sample and sample preparation processing information on the sample from the operation center to the observation center, executing preparation processing of the sample in the observation center, displaying an observation image obtained based on observation condition information including the preparation processing of the sample and by remote operation from the operation center on the two image display units, and executing charge processing based on a content level of the observation including the preparation processing of the sample and occupying hours of the electron microscope, and further displaying the processing result.

According to the system and the method described above, a client can obtain an image by operating as if the client owned an electron microscope such as a TEM always under the best condition of the equipment without installing the equipment and without performing maintenance of the equipment. Further, since the client can ask the observation center side to perform preparation of the sample, the client can not only keep his working place safe and clean, but can smoothly obtain image information under an accurate operation condition because the client can receive consultation advice from a person of the observation center side skilled in the operation.

BEST MODE FOR CARRYING OUT THE INVENTION

An embodiment in accordance with the present invention will be described below, referring to the accompanied drawings.

Figure 1:
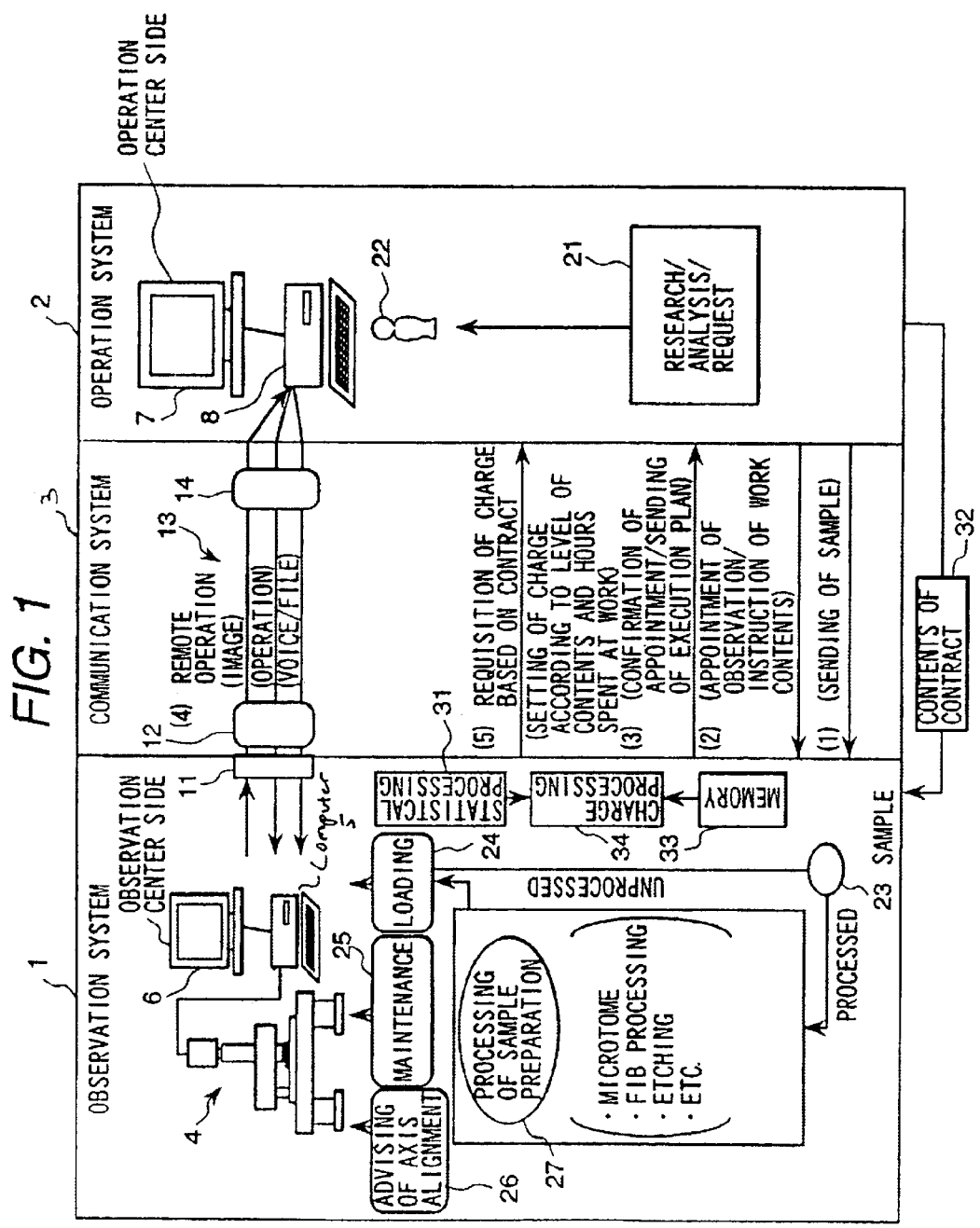
FIG. 1 is a block diagram showing the structure of an embodiment in accordance with the present invention.

FIG. 1 is a block diagram showing the structure of an embodiment in accordance with the present invention.

The electron microscope observation system in accordance with the present invention is composed of an observation system 1 having an electron microscope installed, an operation system 2 for performing remote operation of the electron microscope and a communication system 3 for connecting both with digital communication.

As the electron microscope, a TEM (a transmission electron microscope), a SEM (a scanning microscope) an electron probe micro-analyzer are typical, but here description will be made taking the TEM 4 as an example.

The observation system 1 is owned by an observation center side (an equipment supplier side) of a manufacture/dealer or a lender of the TEM 4. The operation system 2 is owned by an operation center side (a client side) of a user. The operation system 2 itself may be owned by the observation center side.

An existing communication system, for example, a telephone (ISDN) line, a wireless line or the Internet may be used as the communication system 3.

The facility and the equipment for sending and receiving digital image signals may be owned by the observation center side.

The observation system 1 comprises the TEM 4 described above, a computer an (electronic terminal) 5 as an information processing unit and an image display unit 6 such as a TV receiver or the like, and the TEM 4 is controlled by the computer 5, and the screen display on the image display unit 6 is also controlled by the computer 5.

The operation system 2 comprises an image display unit 7 such as a TV receiver or the like and a computer 8 (an electronic terminal), and the image display unit 7 is controlled by the computer 8.

The observation system 1 displays image information obtained from the TEM 4 on the image display unit 6, and the image information is converted to signals suitable for transmission by a converting unit 11 and then converted to digital signals by an analogue-digital converter 14 to be output to a transmission path 13. A digital-analogue converter 14 receives the digital signals from the transmission path 13, and converts the digital signals to an analogue signals to display on the image display unit 7. The digital signals may be used so as to be directly displayed. In the case of the TEM, a TV camera for converting the image to electric signals is used. The signals converted to video signals by the converting unit 11 are converted to digital data to be sent to the transmission path 13.

As the analysis client of the operator in the operation system side observes the sample and controls changing the observation position, the magnification and so on by using the TEM 4 of the observation system 1 through the communication system 3, the image is displayed on the image display unit 7 of the operation system 2 installed at a remote place, and the analysis client can observe the image on the image display unit 7 at hand. The analysis client can directly obtain a desired image at hand by selecting an image to be analyzed having a required position and a required magnification using the computer 8 and by taking a photograph of the image using the operation system 2. The instruction information directly operated by the analysis client is transmitted as digital signals through the transmission path 13 to be able to perform the movement operation of the sample stage, the changing operation of the magnification and the focusing operation.

Description will be made below on the method that the analysis client performs by observation of the desired image having a position and a magnitude to be analyzed using the TEM of the observation center side without installing the equipment such as the TEM.

A request of research and analysis 21 on a sample at hand is proposed from a person in charge in the client side. An analysis client 22 of the client side is notified of the request. The analysis client 22 (1) sends a sample to be observed to the observation center side as a sample 23, and (2) makes an observation appointment and an instruction of work contents for use of the TEM using the transmission path 13. Conditions of preparation processing of the sent sample 23 is transmitted in a form of image in order to secure the accuracy. How the sample 23 should be preparation-processed is one of the important factors for the analysis client. In a case where a large number of and various kinds of instruments such as TEMs are installed in the observation center side, the analysis client makes an appointment by notifying the observation center side of a desired TEM to be used. The observation center side performs the approval and the confirmation of appointment, and notifies the analysis client 22 of the contents of execution plan using the transmission path 13.

If the analysis client 22 agrees to (approves) the contents of the execution plan, the observation center side classifies the sample based on a level of the contents of observation and the condition of the preparation processing transmitted whether the sample is observed with or without preparation processing. In the case where the sample is observed without sample preparation processing, the sample is directly loaded 24 into the TEM. In the case where the sample is observed with sample preparation processing, the sample preparation processing 27 is performed according to the instruction. The condition of the sample preparation processing can be satisfied by microtome, FIB processing, etching or the like depending on the level of observation contents. As described above, the preparation-processed sample is loaded 24 into the TEM. The observation center side performs maintenance 25 of the TEM and performs advice 26 of axial alignment. When the sample is loaded into the TEM, the observation center side notifies the analysis client 22 that the observation is ready. (4) The analysis client 22 remotely operates an electron microscope operating apparatus provided to the TEM 4 using the computer B and further using the computer 5 to perform observation of the preparation-processed sample by setting the position to be analyzed and the magnification. This operation is executed in a form of operation command or voice/file command through the transmission path 13.

An image observed by the TEM 4 is displayed on the image display unit 6 as described above, and the image display unit 7 through the transmission path 13 as the same picture. Since the observed image is displayed as the same picture, the operation instruction of the analysis client 22 can be appropriately executed.

The occupying hours of the TEM for the observation, that is, the analysis hours are statistically processed to add up occupying hours (statistical processing 31). Further, a charge system corresponding to content levels of the sample preparation processing is determined by the contents of contract 32, previously agreed, and the contents are stored 33 in a memory unit, not shown. The content levels are input to a processing means of the computer 5 corresponding to the contents of observation. The computer 5 executes charge processing 34 for demanding the charge according to the content level and the occupying hours. Therefore, a charge processor is provided. The cost required for maintenance of the equipment and the advice of axis alignment are reflected to the contents of contract 32. Furthermore, whether the observation system 1 or the operation system 2 is owned by the observation center side or the client side and the analysis working period are reflected to the contents of contract. The urgency of the analysis may be reflected to the contents of contract.

Figure 2:
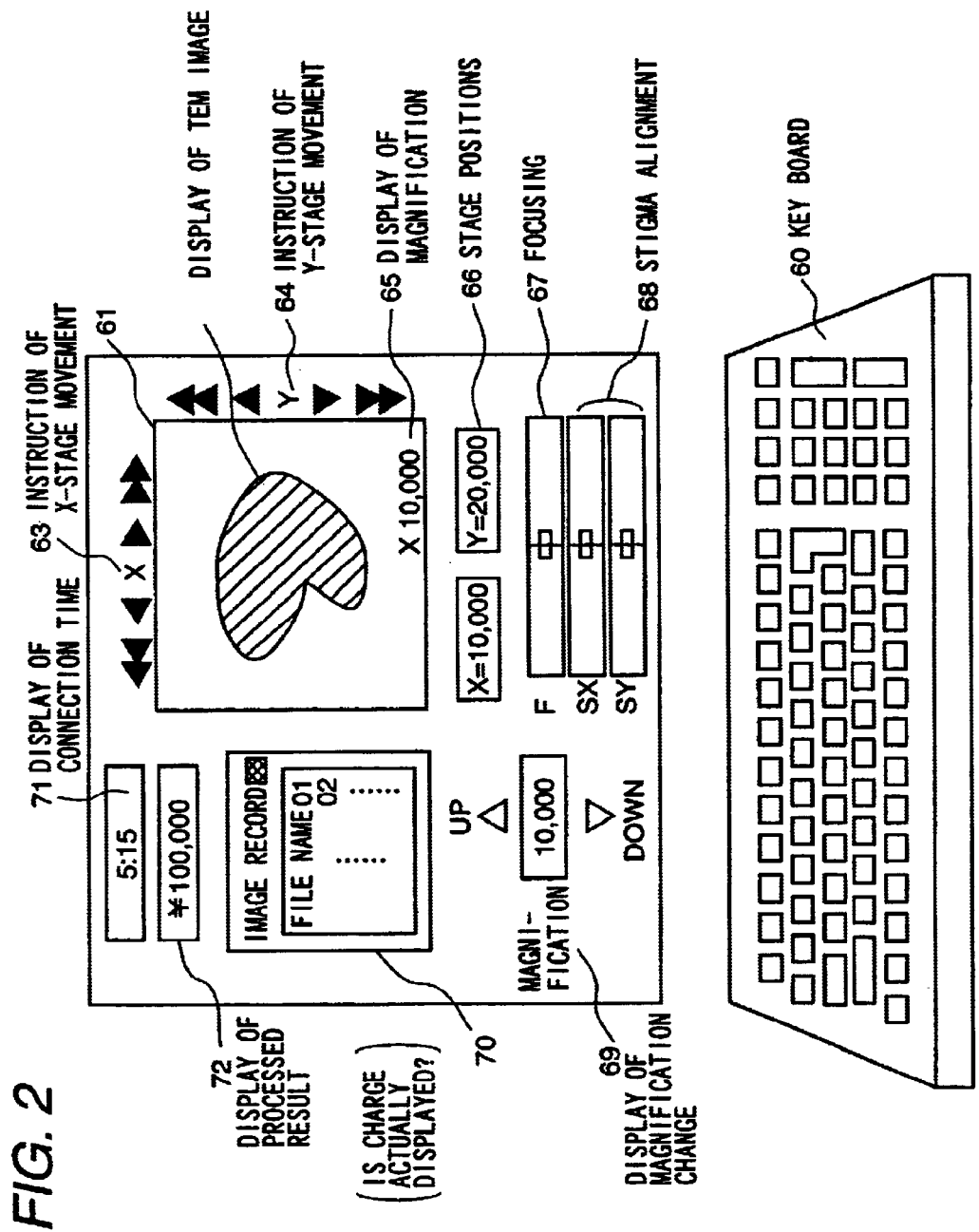
FIG. 2 is a view showing the outer appearance of an image display unit.

FIG. 2 shows the image display unit 6 or 7 installed in the observation center side or in the operation center side in a case where the transmission path such as ISDN or the like is used. On a screen 61, the contents of screen for executing the appointment and the approval of observation through a keyboard 60 are displayed, and display of a TEM image is also displayed. An X-stage movement instruction portion 63 and a Y-stage movement instruction portion 64 are arranged in an upper portion and a side portion of the screen 61, respectively. Further, a magnification display 65 is also arranged in the screen 61. Stage position display portions 66 are also arranged in a lower portion of the screen 61. Further, a focusing portion 67 and a stigma alignment portion 68 are arranged at positions under the stage position display portions 66. A magnification change display portion 69 is arranged beside the focusing portion 67 and the stigma alignment portion 68. In the configuration described above, the appointment and the approval of observation are performed according to the items displayed on the screen 61, and the transmission of the observation information conditions including sample preparation processing conditions to the image display unit 6 of the observation center is also performed by displaying the information on the screen. An image record portion 70 is arranged in a side portion of the screen 61 so as to display recorded file names. A connection time display portion 71 for displaying occupying hours of the TEM is arranged in an upper portion of the screen, and a processed result display portion 72 for displaying a result of the charge processing, for example, for displaying a rank or directly a charge for use is arranged under the processed result display portion 72. The connection time is the occupying hours of the electron microscope. Instead of the connection time actually measured, an amount of consumed electric power or number of images may be displayed, but the hours spent at analysis work here includes the amount of consumed electric power or number of images.

By connecting the image display units 6 and 7 to each other through the transmission path 13, for example, through ISDN, the TEM image can be displayed on both of the image display units 6 and 7 almost in real time.

Figure 3:
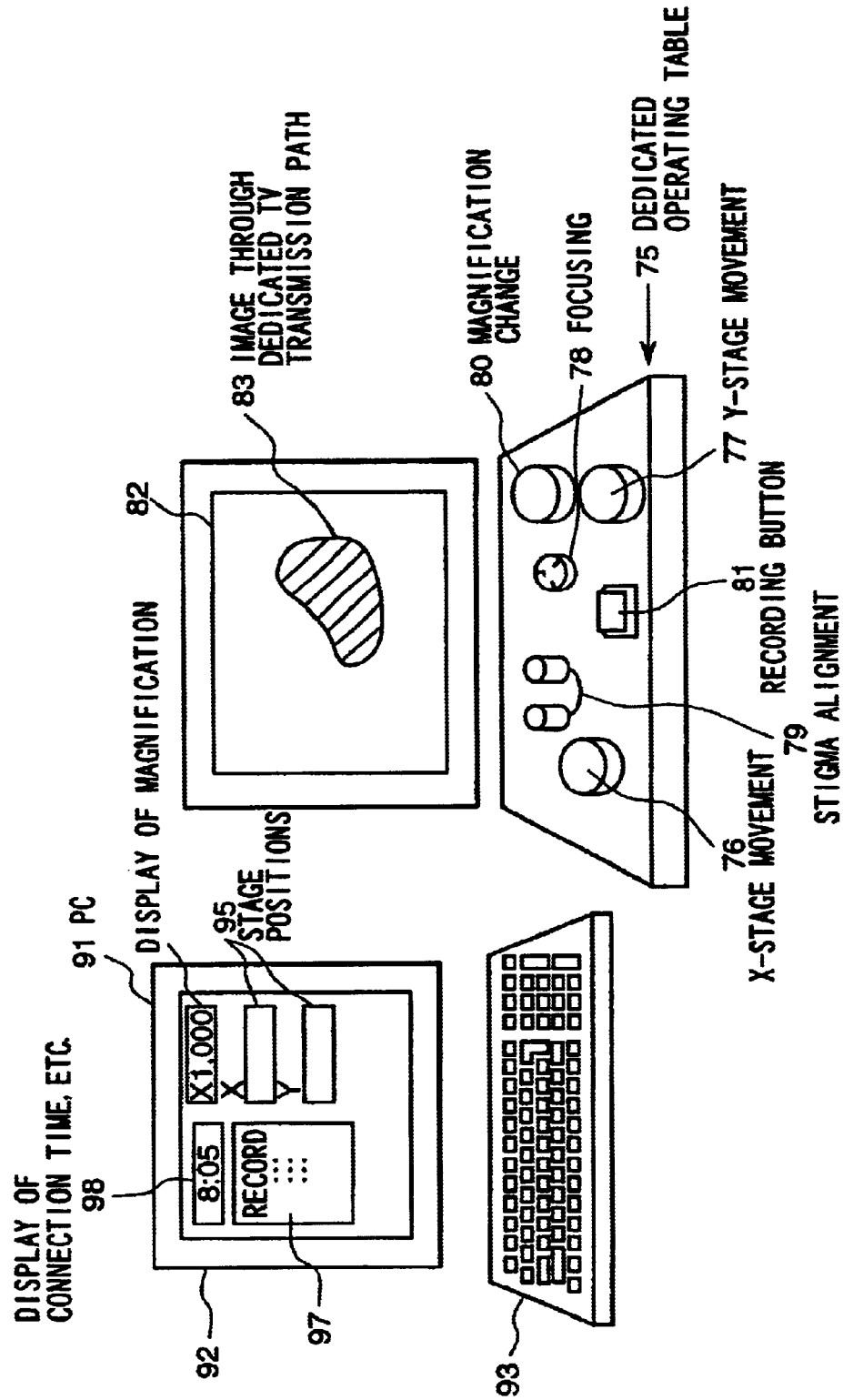
FIG. 3 is a view showing the outer appearance of the image display unit and a PC.

FIG. 3 shows the image display units 6 or 7 installed in the observation center side or in the operation center side in a case where a dedicated transmission path of image-only use is provided. A dedicated operating table 75 comprises an X-stage movement instruction portion 76, a Y-stage movement instruction portion 77, a focusing portion 78, a stigma alignment portion 79, a magnification change instruction portion 80 and a recording button 81. A sample tilting instruction portion and a rotation instruction portion may be arranged. An image 83 transmitted through a dedicated TV transmission path is displayed on a screen 82.

A personal computer 91 is composed of a main body portion 92 and a keyboard 93, and a stage position display 95, a magnification display, an image record display 97 and a connection time display and/or a charge processing result display 98 are arranged in a screen.

As described above, by providing the dedicated transmission path of image-only use, the TEM image can be displayed on the image display units 6 and 7 in real time.

Figure 4:
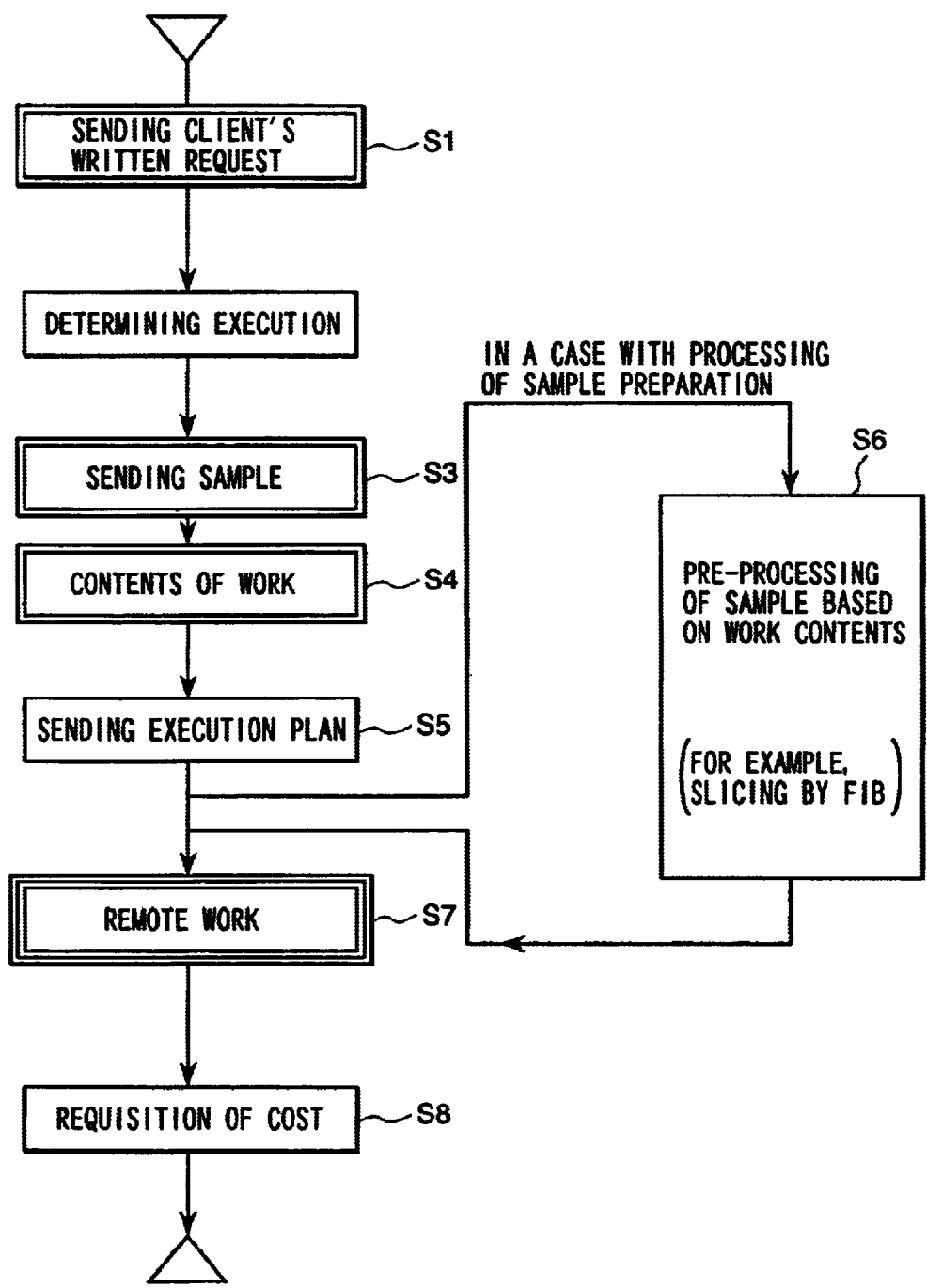
FIG. 4 is a flowchart.

FIG. 4 shows the flow in a case where observation is performed using the TEM as a single instrument. In the figure, the double frame box indicates the operation center (the client side), and the single frame box indicates the observation center. The triple frame box indicates both.

Referring to the figure, a written request of the client is electronically transmitted from the operation center (S1), and the observation center side determines an execution of observation based on the written request. A sample is sent to the observation center based on the determination (S3), and contents of the work, for example, observation information conditions including a condition of sample preparation processing such as a magnification instruction, a sample tilting instruction, a rotation instruction and so on are instructed (S4). The observation center side electronically transmits the contents of execution plan (S5), and then the remote work is started. The remote work is basically proceeded by operating the computer 8 in the operation center side, but the observation center side cooperates with the operation center side if necessary (S7). In a case of requiring sample preparation processing, the preparation processing (for example, slicing by FIB) of the sample is performed (S6), and the remote work is performed for the preparation-processed sample (S7). An obtained image is electronically transmitted to the operation center side at once, and at the same time the charge processing based on the content level and the occupying hours of the TEM is executed to make requisition of the cost (S8). By doing so, the necessary observation of the sample can be performed without installing the TEM in the operation center side.

As well known, the preparation of TEM sample through the FIB (focused ion beam) method can fabricate a TEM sample of a specified position having a high space resolution of micrometer order.

Figure 5:
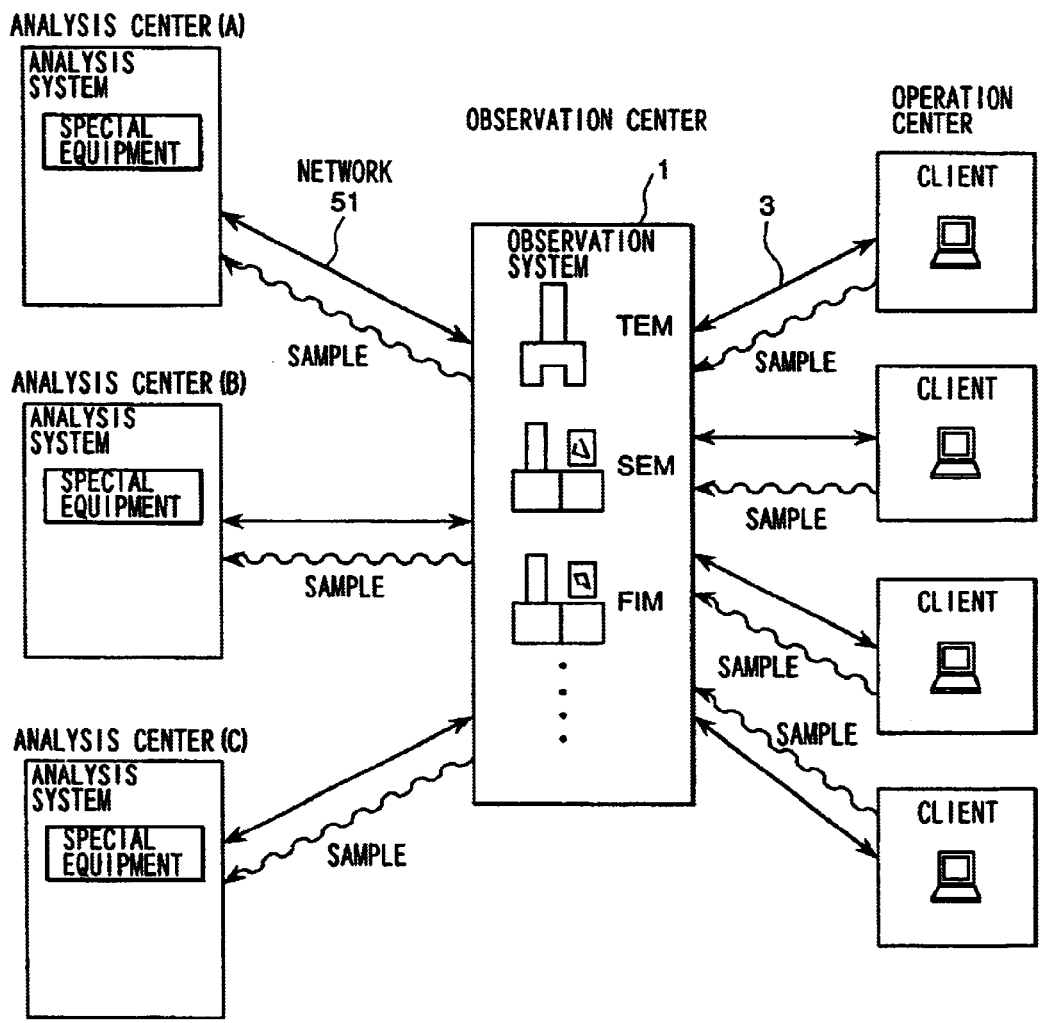
FIG. 5 is a diagram showing the network of the electron microscope observation system

FIG. 5 is a block diagram showing the structure of an example in which the electron microscope observation system is networked. In this example, the observation system 1 in the observation center comprises a large number of electron microscopes such as TEMs, SEMs, FIBs (here, the FIB is included in the concept of the electron microscope). Number of the instruments is set corresponding to number of clients. Further, the observation center is connected by network 51 to analysis centers (A), (B), (C) which comprise special equipment, for example, an X-ray analysis apparatus, an Auger analysis apparatus, a mass spectrometer or an ultra high voltage electron microscope. By doing so, the observation center supplies a sample to the analysis center to request the analysis. Therefore, the observation center can provide the operation center through the communication system 3 with the results from the analysis center together with an image obtained from the electron microscope.

From the observation center's viewpoint, the embodiment in accordance with the present invention provides the following observation system and the following observation method. That is, the embodiment in accordance with the present invention provides the observation system in which the appointment of observation and approval screen is displayed on the image display unit 6, the sample preparation-processed in the observation center side based on the instruction given from the operation center through the transmission path being loaded, the observation being executed based on the sample observation condition information, the image information being output, the observation image being displayed on the image display unit 6, the charge processing being executed based on the content level of observation including the preparation processing of the sample and the occupying hours of the electron microscope, the result of the charge processing being displayed. The content level includes, in addition to the level of the observation, the initial investment of the electron microscope, the ownership, the magnification, the required degree of man-hours, and includes even the concept of the role sharing that images up to a specified number are obtained by the observation center side, but the other images of additional number are obtained by the operation center side.

The embodiment in accordance with the present invention provides the observation method which comprises the steps of displaying the appointment of observation and approval screen on the image display unit 6, receiving the sample and the sample preparation processing information sent from the operation center, performing preparation processing of the sample, displaying the observed images obtained based on the observation condition information including the preparation processing of the sample and by remote operation from the operation center on the image display unit, and executing the charge processing based on the content level of observation including the preparation processing of the sample and the occupying hours of the electron microscope to display the result of the charge processing.

From the operation center's viewpoint, the embodiment in accordance with the present invention provides the following observation system and the following observation method. That is, the embodiment in accordance with the present invention provides the observation system in which the appointment of observation and approval screen is displayed on the image display unit 7, the conditions of the sample preparation processing performed in the observation center side being instructed through the transmission path, the image information being output by performing observation based on the sample observation condition information, the observation image being displayed on the image display unit 7, a result of the charge processing being displayed, the result being obtained by executing the charge processing based on the content level of observation including the preparation processing of the sample and the occupying hours of the electron microscope.

The embodiment in accordance with the present invention provides the observation method which comprises the steps of displaying the appointment of observation and approval screen on the image display unit 7, sending the sample and the sample preparation processing information of the sample from the operation center to the observation center, instructing the observation center to perform the preparation processing of the sample, displaying the observation images obtained based on the observation condition information including the preparation processing of the sample and by operation from the operation center on the image display unit, displaying a result of the charge processing which is obtained by executing the charge processing based on the content level of observation including the preparation processing of the sample and the occupying hours of the electron microscope.

What is claimed is:

1. A sample observation method of observing a sample on the basis of an electron microscope and electrons obtained by irradiating electrons on the sample using the electron microscope, comprising the steps of:

instructing a reservation of observation in which the electron microscope is used from an operation center to an observation center via a transmission circuit, transmitting that said sample is provided on said microscope, and a preparation of observation is completed from the observation center to the operation center, setting the magnification and the position to be observed of the sample by a remote control from said operation center, and displaying an image of said sample on screen display units in said observation center and said operation center.

2. The sample observation method according to claim 1, wherein axis adjustment advice is given from said observation center to said operation center.

3. The sample observation method according to claim 1, wherein an operation instruction to said electron microscope is given from said observation center to said operation center on the basis of the sample image displayed in said screen display units.

4. An electron microscope observation system comprising:

an electron microscope;

an image display unit provided on a side of the electron microscope, which displays an image signal obtained by irradiating electrons on a sample using the electron microscope;

a transmission path used for transmitting an image signal; and an image display unit provided on a side of an operation center, which displays a screen of the electron microscope using the image signal, for performing shift operation, magnification-change operation and focusing operation of a sample stage of the electron microscope, wherein a reservation of said sample to said electron microscope is transmitted from said observation center to said operation center via said transmission path, the position and the magnification of said sample to be analyzed is set by remote control from said operation center, and the image of said sample is displayed on the screen display unit of each of said observation center and said operation center.

5. The electron microscope observation system according to claim 4, wherein axis adjustment advice is given from said observation center to said operation center via said transmission path.

6. The sample observation method according to claim 1, wherein an operation instruction to said electron microscope is given from said observation center to said operation center on the basis of the sample image displayed in said screen display unit.

* * * * *